United States Patent [19]

Bender et al.

[11] Patent Number: 5,008,390

[45] Date of Patent: Apr. 16, 1991

[54] COMPOUNDS FOR PREPARING 6-PHENYL-2,3-DIHYDROIMIDAZO[2,1-B]-THIAZOLES AND CORRESPONDING THIAZINES

[75] Inventors: Paul E. Bender, Cherry Hill; Ivan Lantos, Blackwood, both of N.J.; Michael A. McGuire, Norristown, Pa.; Lendon N. Pridgen, Audubon, Pa.; Herbert B. Winicov, Blue Bell, Pa.

[73] Assignee: SmithKline Beckman Corporation, Philadelphia, Pa.

[21] Appl. No.: 266,728

[22] Filed: Nov. 3, 1988

Related U.S. Application Data

[60] Division of Ser. No. 856,246, Apr. 28, 1986, Pat. No. 4,803,279, which is a continuation-in-part of Ser. No. 737,137, May 23, 1985, abandoned, which is a continuation-in-part of Ser. No. 808,595, Dec. 12, 1985, abandoned.

[51] Int. Cl.$^5$ .............................................. C07D 513/04
[52] U.S. Cl. ...................................... 546/199; 544/48; 548/154; 548/155
[58] Field of Search .......................... 546/199; 544/48; 548/155, 154

[56] References Cited

U.S. PATENT DOCUMENTS 4,175,127 11/1979 Bender et al. ...................... 546/271

FOREIGN PATENT DOCUMENTS 0000353 1/1979 European Pat. Off. .

OTHER PUBLICATIONS

D. L. Comins, *Tetrahedron Letters* 24 (1983).
K. Akiba et al., *Tetrahedron Letters* 23, 429 (1982).
D. L. Comins et al., *J. Org. Chem.* 47, 4315 (1982).
*Chemical Abstracts*, vol. 78, No. 25, pp. 418–419, 159620j (1973).

*Primary Examiner*—Jane T. Fan
*Attorney, Agent, or Firm*—Dara L. Dinner; Edward T. Lentz; Stuart R. Suter

[57] ABSTRACT

6-Aryl-2,3-dihydroimidazo[2,1-b]thiazoles and corresponding thiazines act as nucleophiles, either directly or in the form of Grignard reagents, with N-acylpyridinium salts to produce new 6-aryl-5-(N-acyl-1,4-dihydro-4-pyridyl)-2,3-dihydroimidazo-[2,1-b]thiazoles and corresponding thiazines. These are oxidized to give the corresponding pyridyl-substituted imidazo[2,1-b]thiazoles and thiazines, which are active as inhibitors of the 5-lipoxygenase pathway of arachidonic acid metabolism.

5 Claims, No Drawings

COMPOUNDS FOR PREPARING 6-PHENYL-2,3-DIHYDROIMIDAZO[2,1-B]-THIAZOLES AND CORRESPONDING THIAZINES

This is a division of application Ser. No. 06/856,246 filed Apr. 28, 1986 now U.S. Pat. No. 4,803,279 issued Feb. 7, 1989, which is a continuation-in-part of application Ser. No. 06/737,137 filed May 23, 1985, now abandoned, which is a continuation-in-part of Ser. No. 06/808,595 filed Dec. 12, 1985, now abandoned.

BACKGROUND OF THE INVENTION

This invention relates to new intermediates and processes for preparing 5-(4-pyridyl)-6-phenyl-2,3-dihydroimidazo[2,1-b]thiazoles and corresponding thiazines which have activity as inhibitors of the 5-lipoxygenase pathway of arachidonic acid metabolism.

Certain anti-arthritic 5,6-diaryl-2,3-dihydroimidazo[2,1-b]thiazoles are described in U.S. Pat. No. 4,175,127. The method disclosed therein for preparing them includes a ring closure of the corresponding 4,5-diaryl-2-mercaptoimidazole. If the substituents at the 4,5-positions of the 2-mercaptomidazole are different, the position isomers at the 5,6-positions of the end product 2,3-dihydroimidazo-[2,1-b]thiazoles are produced in about equal quantities. In most cases, and certainly with the preparation of the preferred 5-(4-pyridyl)-6-(4-fluorphenyl)-2,3-dihydroimidazo-[2,1-b]thiazole, the position isomers are separated with difficulty, and even the most efficient separation techniques, preferably using column separation, provide less than 50% yield of the preferred isomer. In practical fact, however, overall yields are much lower. The present invention greatly reduces the cost of chemical for the preparation of the biologically active 5-pyridyl-6-aryl compounds.

Direct addition of various organic moieties to a pyridine ring through the use of Grignard reagents or other organometallic salts is known. For example, it is shown by K. Akiba et al., *Tetrahedron Letters*, 23, 429 (1982), that 4-alkylpyridines can be prepared with high regioselectivity by reacting a 1-acylpyridinium salt with an alkylcopper-boron trifluoride complex. The synthesis of 1-acyl-4-alkyl(or aryl)-1,4-dihydropyridines by reacting the appropriate alkyl or aryl Grignard reagent with 1-acylpyridinium salt, in the presence of cuprous iodide, is shown in Comins, *Tetrahedron Letters*, 24, 2807 (1983) and Comins et al, *J. Org. Chem.*, 47, 4315 (1982).

Direct addition of imidazo-thiazole or -thiazine moieties to pyridine, however, has not been previously shown by these methods. The fused-ring Grignard reagents necessary for direct addition to the pyridinium salt have heretofore been unavailable. Nor has it been suggested previously that a 6-phenyl-imidazo[2,1-b]thiazole (or the corresponding thiazine), by acting as a nucleophile at its 5-position, could bypass the metallic intermediate entirely and add directly to pyridine, particularly with selectivity for the 4-position. The present invention, however, provides methods by which this direct regiospecific addition of the fused-ring moiety can be effected, either by direct nucleophilic attack or by use of novel Grignard intermediates. Accordingly, the present invention avoids the yield loss resulting from the prior art's production of 5,6-position isomers during ring-closure of the corresponding mercaptoimidazole.

SUMMARY OF THE INVENTION

The present invention relates to new compounds having the basic structure of a 5-(N-acyl-1,4-dihydro-4-pyridyl)-6-phenyl-2,3-dihydroimidazo[2,1-b]-thiazole or the corresponding thiazine (compounds of Formula I) and to two processes for preparing such compounds:

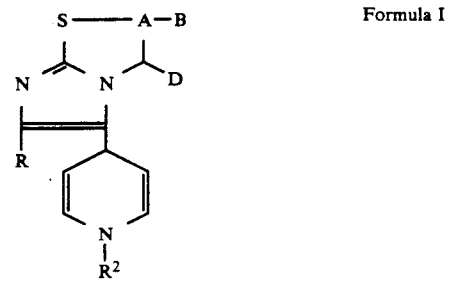

Formula I in which:
A is —CH$_2$— or —CH$_2$CH$_2$—;
B and D are independently H, methyl, ethyl, or dimethyl;
R is
  (a) phenyl;
  (b) monosubstituted phenyl wherein the substituent is halogen, C$_1$–C$_3$ alkoxy, C$_1$–C$_3$ alkylthio, C$_1$–C$_4$ alkyl, CF$_3$, 2,2,2-trihaloethoxy, prop-2-ene-1-oxy, C$_1$–C$_3$ dialkylamino, N-(C$_1$–C$_3$ alkyl)-(C$_1$–C$_3$ alkanamido), or N-azacycloalkyl of 5 or 6 carbon atoms;
  (c) disubstituted phenyl wherein the substituents are independently C$_1$–C$_4$ alkyl or C$_1$–C$_3$ alkoxy, or the substituents together form a methylenedioxy group; or
  (d) 3,4,5-trimethoxyphenyl;
R$^2$ is H or

and
R$^1$ is C$_1$–C$_8$ alkyl, C$_1$–C$_8$ alkoxy, phenyl, phenoxy, benzyl, or benzyloxy.

The processes of the present invention by which the Formula I compounds are prepared involve nucleophilic addition to a 1-acylpyridinium salt. In one of these processes, a 6-phenyl-imidazo[2,1-b]thiazole or the corresponding thiazine is reacted directly with the pyridinium salt. In the other process, the imidazothiazole (or thiazine) is converted to its corresponding Grignard reagent prior to reaction with the pyridinium salt. Another aspect of the present invention provides the novel Grignard reagents themselves and a method by which they are prepared. In yet another aspect of the present invention, a method of oxidizing the dihydropyridine compounds of Formula I to their pyridyl derivatives, which have activity as inhibitors of the 5-lipoxygenase pathway of arachidonic acid metabolism activity, is provided.

DETAILED DESCRIPTION OF THE INVENTION

This invention relates to new intermediates and processes for preparing biologically active final products which are 5-(4-pyridyl)-6-phenyl-2,3-dexydroimidazo[2,1-b]thiazoles and thiazides (hereinafter referred to as "biologically active final products"). All of the biologically active final products have activity as in vivo inhibitors of the 5-lipoxygenase pathway of arachidonic acid metabolism in animals, such as man and other mammals, and some are also useful a intermediates in the preparation of compounds which have activity as in vivo inhibitors of the 5-lipoxygenase pathway in animals such as man and other mammals (as disclosed in Bender et al., U.S. Ser. No. 808,595, filed Dec. 12, 1985 and Bender et al., U.S. Ser. No. 856,875, titled "Inhibitors of the 5-Lipoxygenase Pathway", filed simultaneously with the subject application, the disclosure of both of which is hereby incorporated by reference), and some of the biologically active final products also have activity as inhibitors of the cyclooxygenase pathway of arachidonic acid metabolism (as disclosed by their activity in the adjuvant arthritic rat model in Bender et al., U.S. Pat. No. 4,175,127, the disclosure of which is hereby incorporated by reference).

Compounds of Formula I are prepared according to one aspect of this invention by reaction (A):

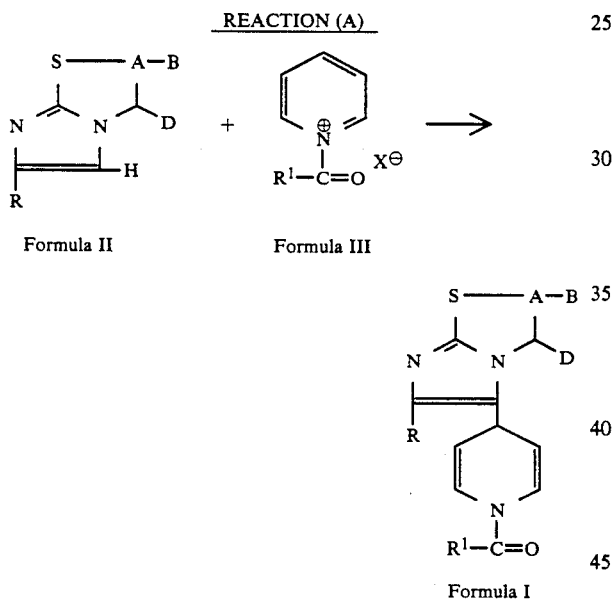

in which:
- A, B, D, and R are as described above;
- $R^1$ is the non-reactive residue of a reactive acyl ester, especially an acyl halide, such as $C_1$–$C_8$-alkyl, $C_1$–$C_8$-alkoxy, phenyl, phenoxy, benzyl or benzyloxy; and
- X is an anion commonly associated with acyl cations or equivalent to the same. Particularly useful is a reactive halogen such as iodo, chloro or bromo. Other anions are acetate, propionate, triflate (trifluoromethylsulfonate), tosylate (p-toluenesulfonate), mesylate (methylsulfonate) or boron tetrafluoride.

The starting materials for this process for Formula II compounds in which $A = CH_2$ (thiazole) are described in S. Kano, Yakugaku Zasshi, 92 51–58 (1972), which, in general, describes that 6-phenyl-2,3-dihydroimidazo[2,1-b]thiazoles can be prepared by heating the corresponding 2-amino-4,5-dihydrothiazole with the appropriately substituted phenacyl bromide in an organic solvent, followed by treatment with an alkali such as NaOH to recover the compound from its hydrobromide.

Starting materials for Formula II compounds in which A is $CH_2$–$CH_2$ (thiazine) can be prepared in an analogous manner to the Kano process, described above, from the corresponding 2-amino-5,6-dihydro-4H-1,3-thiazine. More particularly, 7-(4-substituted phenyl)-2,3-dihydro-4H-imidazo [2,1-b]-(1,3)thiazines can be prepared by reacting the corresponding 2-amino-5,6-dihydro-4H-1,3-thiazine with 4-substituted bromoacetophenones in a non-polar solvent such as benzene or chloroform, to form an intermediate which is then refluxed in water. See, Schoeberl, et al., *Justus Liebigs Ann. Chem.*, 742, 85–97 (1970). It has also been found that a polar solvent can be used as well, and that the intermediate may or may not be isolated prior to the refluxing step. The amino-thiazine starting material can be prepared by treating 3-bromopropylamine with t-butyl isothiocyanate, followed by reflux treatment with HBr or HCl. See, for example, Schubert, et al., *Arch. Pharm.*, 301(10), 750–762 (1968).

The reaction (A) is carried out by reacting the 6-arylimidazo[2,1-b]thiazole or thiazine analog of Formula II with an excess of both the pyridine and the reactive acyl ester reactant in an organic solvent in which the reactants ar soluble and with which the reactants, especially the acyl ester, are inert. One skilled in the art will recognize that the pyridine and acyl ester react to form the acylpyridinium reagent of Formula III in situ. Optionally, the acylpyridinium reagent can be prepared separately in a solvent and then added to the solution of Formula II compound. Suitable solvents include methylene chloride, ethylene chloride, chloroform, carbon tetrachloride, tetrahydrofuran, ethyl ether, dioxane, toluene, or excess pyridine.

In the conduct of reaction A, the reaction mixture is cooled during the mixing of the reactants, preferably to a temperature between 5°–20° C., by use of an ice/water bath. The mixture is then allowed to stand briefly at ambient temperature, followed by refluxing until reaction is complete. The reaction mixture is continually assayed using high performance liquid chromatography (HPLC) or thin layer chromatography (TLC) on aliquots to ascertain if unreacted Formula II compound is present. If so, additional acyl pyridinium salt is introduced. Other conditions of the reaction are standard to the art. Following the reaction, the resultant Formula I compounds can be recovered from the reaction mixture and isolated by standard techniques, or the reaction mixture (with no isolation of the Formula I compounds) can be used as the medium for the oxidation step described below as reaction (D).

Compounds of Formula I wherein $R^2$ is

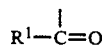

can be prepared according to another aspect of this invention by reaction (B):

REACTION (B)

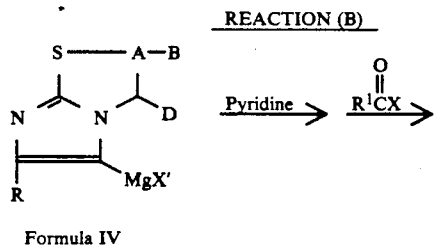

Formula IV

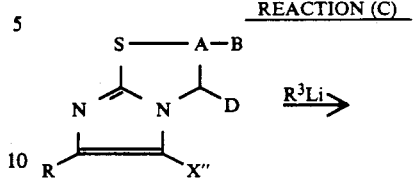

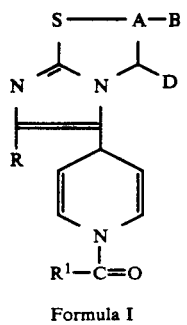

Formula I in which X' is Cl, Br, or I (preferably Br); and R, R¹, X, A, B, and D are as described earlier, provided, however, that R is other than N-($C_1$-$C_3$ alkyl) however ($C_1$-$C_3$ alkanamido) phenyl.

Reaction (B) is conducted by contacting the Grignard reagent (Formula IV) with an excess of both the pyridine and the selected reactive acyl ester in a solvent appropriate for Grignard-reagent use. Examples of such solvents include, but are not limited to, dry ethers such as ethyl ether, or preferably, tetrahydrofuran. The Grignard reagent can be combined with the pyridine and the acyl ester in sequence, or as in reaction (A) above, the pyridinium salt can be prepared separately and then added to the solution of Grignard reagent. Preferably, the reaction is conducted by the addition of 2-6 moles of pyridine to each mole of the Grignard reagent, followed by addition of at least an equimolar amount of the acyl compound.

In the conduct of reaction (B), the reactants are mixed into the solvent, with cooling, preferably to a temperature of −10° C. or below. During the mixing period, at least about 5 mole % of cuprous iodide (CuI), based on the molar quantity of pyridine present, is introduced to the reaction mixture to insure the ultimate addition of the Grignard reagent at the 4-position of the N-acyl-1,4-dihydropyridine compound.

When the reactants have been thoroughly dissolved, the reaction initiates autogenously and the mixture can be permitted to warm to a temperature of about 20° C., but preferably no higher than about 15° C. Aliquots of the reaction mixture are extracted continuously and assayed using HPLC or TLC to determine the presence of unreacted imidazo[2,1-b]thiazole or thiazine. The conditions of the reaction are otherwise standard for those pertaining to Grignard synthesis in general. As with the Formula I compounds prepared by reaction (A), recovery and isolation can be effected by standard techniques, or the reaction mixture (without isolation of the Formula I compounds) can be used as the medium for the oxidation step of reaction (D) below.

The Grignard reagents of Formula IV are novel compounds which embody another aspect of this invention.

The Formula IV reagents are prepared by reaction (C):

REACTION (C)

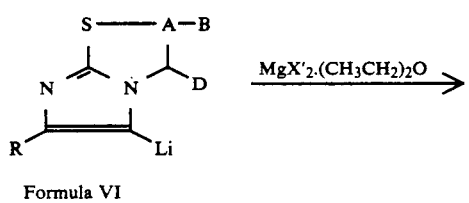

Formula V

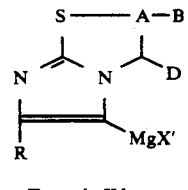

Formula IV in which A, B, D, and R are as earlier defined; X' is Cl, Br, or I, preferably Br; X" is Cl or Br; and R³ is $C_1$-$C_5$ alkyl, preferably butyl and most preferably n-butyl. The reaction (C) is conducted in an ether solvent, preferably tetrahydrofuran, at a temperature below 0° C. More specifically, the halogenated starting compound of Formula V is reacted with at least an equimolar amount of the alkyllithium compound at a temperature of from about −80° C. to about −30° C. Following the lithium-halogen exchange, from which the organolithium compound of Formula VI results, the magnesium halide etherate is added to the mixture in excess and reacted with the organolithium compound of Formula VI, during which the reaction temperature can be permitted to rise to a temperature up to about 0° C., although a reaction temperature below about −10° C. is preferred. The Grignard reagent of Formula IV which is prepared in this manner is preferably used immediately in reaction (B), as described above. This is most easily effected by the addition of cuprous iodide and pyridine, followed by addition of the selected acyl ester to the final reaction mixture of reaction (C).

The starting compounds of Formula V which are used in reaction (C) can be prepared by halogenating the 6-arylimidazo[2,1-b]thiazole or thiazine of Formula II described above. Halogenation is effected by standard techniques, which in general include treating the Formula II compound with $Br_2$ or $Cl_2$ in a neutral solvent at an elevated temperature. For example, 5-bromo-6-phenyl-2,3-dihydroimidazo[2,1-b]thiazole can be prepared by reacting the unbrominated starting material of Formula II with an equimolar amount of $Br_2$ in methylene chloride at reflux temperature. See, S. Kano, *Yakagaku Zasshi*, 92, 51–58 (1972).

Irrespective of which reaction route, (A) or (B), is chosen, the compounds of Formula I wherein R²  is

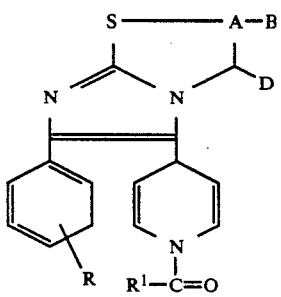

I (Preferred)

are preferably prepared with the most economical pyridinium salt reagents. Examples of such reagents are those in which $R^1$ is ethoxy, methoxy, methyl, or phenyl.

Overall, the preferred compounds of formula I are as follows:

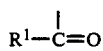

in which $R^1$ is ethoxy, methoxy, methyl, or phenyl; A, B, and D are as described above; and R is H, $C_1$–$C_2$ alkyl, $C_1$–$C_2$ alkoxy, trifluoromethyl, N-azacycloalkyl of 5 or 6 carbon atoms, or halogen, preferably F, Cl, or Br. Most preferable are compounds of the preferred class in which B and D are hydrogen, A is —$CH_2$—(-thiazole), and R is F or Cl, particularly in the 4-position.

In another aspect of the invention, the compounds of Formula I are deacylated and oxidized to form the biologically active final product of Formula VII, as shown in reaction (D):

REACTION (D)

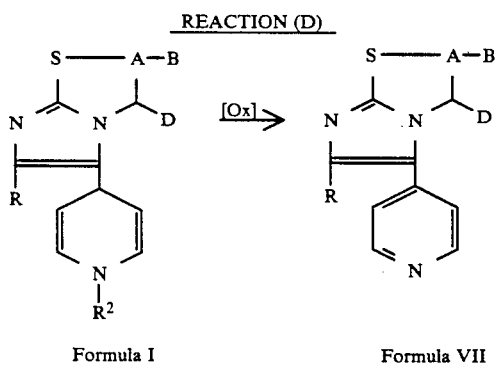

Formula I          Formula VII in which $R^2$ is

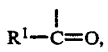

and R, A, B, and D are as defined earlier. Compounds of Formula I in which $R^2$ is hydrogen are intermediates that are formed in situ during the oxidation reaction (D), and as such they are not usually isolated during the reaction sequence, although isolation by standard techniques is possible if desired.

In the conduct of reaction (D), the dihydropyridine of Formula I is reacted with an appropriate oxidizing agent in an inert solvent system until the starting material has been exhausted, as. monitored, for example, by periodic TLC or HPLC analysis. Normally, the oxidizing agent is relatively mild, so as to avoid oxidizing the nuclear nitrogen or sulfur members to their respective oxide derivatives. Exemplary oxidation systems are sulfur ($S_8$) in decalin, tetralin, p-cymene, or xylene as solvent; or chloranil, oxygen gas, manganese oxide, ceric chloride, chromium oxide, hydrogen peroxide or ferricyanide in inert solvents. When the N or S oxide derivatives are the desired end products, a stronger oxidizing agent, such as meta-chloroperbenzoic acid, can be used in excess. Preferred reaction conditions, however, are reaction of a dihydropyridine with sulfur in refluxing xylene or with oxygen in the presence of tert.-butanol/potassium tert.-butoxide.

In general, the oxidation reaction proceeds rapidly, normally within one hour, at a temperature range of from ambient (about 23° C.) for oxygen use, to solution reflux temperature, for sulfur use. The oxidized products of formula VII are isolated and purified using methods standard in the art.

EXAMPLES

The following examples are illustrative, but not limiting of, the operation of this invention. All temperatures are in °C.

EXAMPLE 1

(A)  6-(4-Fluorophenyl)-2,3-dihydroimidazo[2,1-b]thiazole (1 mmol, 220 mg) was placed in a clean, dry flask along with a Teflon-coated stir bar. Tetrahydrofuran (10 ml, distilled from sodium/benzophenone) was added by syringe and stirring was begun. Pyridine (1 ml) was added by syringe. The reaction flask was cooled in an ice/water bath. Ethyl chloroformate (6.3 mmol, 0.60 ml) was added by syringe. The pink heterogeneous solution was allowed to stir for 15 hours. The reaction was then heated to 70° for 45 minutes. The reaction was allowed to cool. The solvent was evaporated off in a rotary evaporator. The residue was treated with 10% potassium carbonate solution (25 ml). The mixture was extracted with methylene chloride (2×100 ml). The separated methylene chloride phase was dried over anhydrous sodium carbonate, filtered and concentrated in a rotary evaporator. The residue was dissolved in methylene chloride (1 ml) and poured into hexane (50 ml). The resulting heterogeneous solution was filtered and concentrated in a rotary evaporator to give 5-(N-ethoxycarbonyl-1,4-dihydro-4-pyridyl)-6-(4-fluoropheny)-2,3-dihydroimidazo[2,1-b]-thiazole, as a thick oil (80 mg, 22%).

(B)  6-(4-Fluorophenyl)-2,3-dihydroimidazo[2,1-b]thiazole (2 mmol, 440 mg) was placed in a flask along with a Teflon-coated stir bar. A mild flow of dry nitrogen was begun and continued throughout the reaction. Pyridine (10 mmol, 790 mg) was added to form a slurry. The reaction vessel was cooled in an ice bath for 5 minutes, then ethyl chloroformate (4 mmol, 0.382 ml) was added over a 1 minute period. The solution solidified. The ice bath was removed and replaced by an oil bath. The oil was heated to 75° over a 45 minute period and then allowed to cool. The product was taken up in methylene chloride (100 ml) and extracted with 5% potassium carbonate solution (50 ml). The aqueous layer was back-extracted with methylene chloride (50 ml). The organic layers were combined, dried over sodium sulfate and filtered. The filtrate was concentrated in a rotary evaporator. The resulting oil was purified by silica gel chromatography (1:1, ether/hexane/2% methanol) to yield the 1,4-dihydro compound (300 mg, 40%) as a white crystalline solid, m.p. 139°–141°.

Anal. Calcd. for $C_{19}H_{18}N_3O_2SF$: C, 61.44; H, 4.88; N, 11.31. Found: C, 61.32; H, 4.77; N, 11.38.

(C) 6-(4-Fluorophenyl)-2,3-dihydroimidazo[2,1-b]thiazole (1 mol, 220 g) was placed in a 5L flask along with a large Teflon-coated stir bar. A light flow of dry nitrogen was passed through the system. Methylene chloride (400 ml) was added and stirring was begun. Pyridine (11.2 mol, 900 ml) was added all at once. The reaction flask was then placed in a large ice bath and stirred for 10 minutes. Ethyl chloroformate (4.35 mol, 354 ml) was charged into an addition funnel and slow dropwise addition was begun. After 1 hour, the addition was complete. After an additional 30 minutes, the ice bath was removed and the mixture worked up.

Methylene chloride (500 ml) was added. The reaction mixture was extracted with water (3×1). The organic layer was concentrated on a rotary evaporator to yield the 1,4-dihydropyridine as a brown solid (380 g, 101%). The solid was recrystallized from hot ethanol to yield the desired 1,4-dihydropyridine in 80% yield (300 g).

(D) A mixture of 51.6 g (0.3 mol) of 4-fluorophenacylchloride, 33.66 g (0.33 mol) of 2-aminothiazoline and 200 ml of ethanol was heated at reflux for 2 hours. The mixture was cooled to room temperature at which point 300 ml of water was added. After a reflux period of 2 hours, the mixture was concentrated to remove about 190 ml of aqueous alcohol. The pH of the residue was adjusted to about 2 with 10% hydrochloric acid (10 ml). The solid product was separated and dried to give 65.4 g (85%) of 6-(4-fluorophenyl)-2,3-dihydroimidazo[2,1-b]thiazole, m.p. 116–118°.

HPLC conditions: $C_{18}$-column, methanol/water/monosodium phosphate, 55:45:0.12%.

The procedure of Section D is used to prepare other 5-hydrogen-6-substituted-imidazo[2,1-b]thiazole starting materials.

EXAMPLE 2

6-(4-Fluorophenyl)-2,3-dihydroimidazo[2,1-b]thiazole (10.0 g, 0.0456 mol) and 11 ml (0.136 mol) of pyridine (previously stirred over potassium hydroxide) were dissolved in 150 ml of methylene chloride. To this cooled solution (10°) was added 17.75 g (0.13 mol) of isobutylchloroformate in 20 ml of methylene chloride under a nitrogen atmosphere. During the addition, the reaction pot temperature was not allowed to rise past 10°. After the addition, the reddish-colored solution was stirred at ambient temperature for 1 hour then heated under reflux for an additional 15 minutes. Thin-layer chromatography (ethyl acetate/hexane/methanol, 15:1:0.1) detected the presence of starting material. An additional 2.13 g (27 mmol) of pyridine, followed by 3.67 g (27 mmol) of isobutyl chloroformate, was added to the reaction vessel. The solution was stirred at room temperature for 1 hour, then, heated to reflux for 15 minutes. Thin layer analysis at this time did not detect starting material. The reaction mixture was diluted with 200 ml of water and extracted with methylene chloride (3×100 ml). The organic layer was dried, then, concentrated to yield 16.0 (85%) of 5-(N-isobutyloxycarbonyl-1,4-dihydro-4-pyridyl)-6-[4-fluoro-phenyl)-2,3-dihydroimidazo[2,1-b]thia zole; m.p. 144°–146° (from acetone/hexane).

Calcd. for $C_{21}H_{22}N_3O_2F$: C, 63.14; H, 5.55; N, 10.52. Found: C, 63.27; H, 5.58; N, 10.49.

EXAMPLE 3

6-(4-Fluorophenyl)-2,3-dihydroimidazo[2,1-b]thiazole(10.0 g, 0.0456 mol) and 11 ml (0.136 mol) of pyridine were dissolved in 150 ml of methylene chloride. To this cooled solution (10°) was added 20.35 g (0.13 mol) of phenyl chloroformate in 20 ml of methylene chloride under a nitrogen atmosphere. During the addition, the reaction pot temperature was not allowed to rise past 15°. After the addition, the reddish-colored solution was stirred at ambient temperature for 1.5 hours, then heated under reflux for an additional 15 minutes. Thin-layer chromatography (ethyl acetate/hexane/methanol, 15:1:0.1) showed the reaction to be complete. The reaction mixture was diluted with 200 ml of water and extracted with methylene chloride (3×100 ml). The organic layer was dried, then concentrated to yield 17.0 g (89%) of 5-(N-phenyloxycarbonyl-1,4-dihydro-4-pyridyl)-6-(4-fluorophenyl)-2,3-dihydroimidazo[2,1-b]thiazole; m.p. 164°–166° (from acetone/hexane).

Calcd. for $C_{23}H_{18}N_3O_2FS$: C 65.86; H, 4.33; N, 10.02. Found: C, 64.84; H, 4.41; N, 9.81.

EXAMPLE 4

6-(4-Fluorophenyl)-2,3-dihydroimidazo[2,1-b]thiazole (45.0 g, 0.204 mol) and 55 ml (0.68 mol) of pyridine were dissolved in 500 ml of methylene chloride To this cooled (ice-water bath) solution (10°) was added 91.3 g (0.65 mol) of benzoyl chloride in 100 ml of methylene chloride under a nitrogen atmosphere. During the addition, the reaction pot temperature was not allowed to rise past 10°. After the addition, the desired product precipitated from solution. The addition of the benzoyl chloride solution was continued. The resulting suspension was stirred at ambient temperature for 15 minutes, then heated to reflux for 15 minutes. Thin-layer chromatography (ethyl acetate/hexane/methanol, 15:1:0.1) showed the presence of some starting material. An additional 20 ml of pyridine followed by benzoyl chloride (28 g, 0.2 mol) were added at room temperature The suspension was stirred for an additional 0.5 hour. Analysis did not detect starting material at this time The reaction suspension was filtered. The collected solid was washed with petroleum ether. The solid was vacuum dried to yield 66.8 g (81%) of 5-(N-phenylcarbonyl-1,4-dihydro-4-pyridyl)6-(4-fluorophenyl)-2,3-dihydroimidazo-[2,1-b]thiazole; m.p. 188°–189°.

Calcd. for $C_{23}H_{18}N_3OFS$: C, 68.47; H, 4.50; N, 10.41. Found: C, 68.34; H, 4.61; N, 10.28.

EXAMPLE 5

5-(N-Ethyloxycarbonyl-1,4-dihydro-4-pyridyl)-6-phenyl)-(4-fluorophenyl)-2,3-dihydroimidazo[2,1-b]thiazole (2.5 g, 6.7 mmol) was suspended in 3 ml of p-cymene and heated to 175° for 0.45 hours with 0.3 g (9.4 mmol) of sulfur. Thin-layer chromatography (ethyl acetate/methanol, 9:1) demonstrated the reaction to be complete at this time. Ethyl acetate (100 ml) was added to the dark solution which was then extracted with 10% hydrochloric acid (3×50 ml). The acidic layer was made basic with aqueous potassium carbonate and extracted with methylene chloride (3×50 ml). The organic layer was, then, dried and concentrated to yield 1.9 g (95%) of crude 5-(4-pyridyl)-6-(4-(fluorophenyl)-2,3-dihydroimidazo[2,1-b]thiazole. Comparison with authentic material by TLC was used to verify the identity of the product; m.p. 189°.

EXAMPLE 6

5-(N-Phenylcarbonyl-1,4-dihydro-4-pyridyl)-6-(4-fluorophenyl)-2,3-dihydroimidazo[2,1-b]thiazole (0.5, 1.2 mmol) was dissolved in 2 ml of tert.-butanol containing 0.7 g (6.2 mmol) of potassium tert.-butoxide. Oxygen was bubbled into the solution which was, then, heated under reflux for 15 minutes. The solvent was, then, removed under vacuum and the residue dissolved in methylene chloride. This organic solution was washed with water (2×50 ml), dried and concentrated to yield 0.4 g (87%) of crude 5-(4-pyridyl)-6-[4-(fluorophenyl)]-2,3-dihydroimidazo[2,1-b]thiazole. This material was assayed by HPLC to be 79.5% pure. This reaction was also carried out in aqueous sodium or potassium hydroxide media.

EXAMPLE 7

Using acetyl bromide and 6-(4-chlorophenyl)-2,3-dihydroimidazo[2,1-b]thiazole in the process of Example 5 gives 5-(N-methylcarbonyl-1,4-dihydro-4-pyridyl)-6-(4-chlorophenyl)-2,3-dihydroimidazo[2,1-b]thiazole.

Using benzyl chloroformate and 6-phenyl-2,3-dihydroimidazo[2,1-b]thiazole gives 5-(N-benzyloxycarbonyl-1,4-dihydro-4-pyridyl)-6-phenyl-2,3-dihydroimidazo[2,1-b]thiazole.

Using methyl chloroformate and 6-(2-methylphenyl)-2,3-dihydroimidazo[2,1-b]thiazole gives 5-(N-methoxycarbonyl-1,4-dihydro-4-pyridyl)-6-(2-methylphenyl)-2,3-dihydroimidazo[2,1-b]thiazole.

Using phenylacetyl chloride and 6-(3-methoxyphenyl)-2,3-dihydroimidazo[2,1-b]thiazole gives 5-(N-benzylcarbonyl-1,4-dihydro-4-pyridyl]-6-(3-methoxyphenyl)-2,3-dihydroimidazo[2,1-b]thiazole.

Using the oxidation conditions of Example 6 for each of these dihydropyridyl compounds gives the respective 5-(4-pyridyl)-6-aryl-2,3-dihydroimidazo[2,1-b]thiazoles.

EXAMPLE 8

4-Acetamidoacetophenone (44 g, 0.25 mole) was suspended in 500 ml methylene chloride and treated with bromine (44 g, 0.275 mole). The reaction mixture was stirred overnight, then evaportated in vacuo. The residue was suspended in 200 ml of absolute EtOH and treated with 2-amino-4,5-dihydrothiazole (60 g, 0.59 mole). The reaction was stirred for 2 days, then taken up in water and extracted with methylene chloride. The organic phase was washed with water and then brine, and then dried over sodium sulfate. Flash column chromatography (silica, eluting with methylene chloride / methanol, 98/2) gave 6-[4-acetamidopheny])-2,3- dihydroimidazo[2,1-b]thiazole.

The above described acetamide (10.2 g, 0.039 mole) was hydrolyzed in refluxing 6N HCl (200 ml) for one hour. The mixture was then cooled and neutralized, and extracted with methylene chloride. The organic layer was washed with brine, dried over sodium sulfate, and evaporated to afford 6.8 g of 6-(4-aminophenyl)-2,3 dihydroimidazo[2,1-b]thiazole.

The above described amine (6.8 g, 0.034 mole) in 150 ml of dimethylformamide was treated with 1,4-dibromobutane (8.4 g, 0.039 mole) and potassium carbonate (15.5 g, 0.11 mole). The reaction mixture was stirred at ambient temperature overnight, and the solvent removed in vacuo. The residue was flash chromatographed (silica, methylene chloride / methanol, 97/3) and the crude product recrystallized from methanol to afford 0.88 g of 6-(4-(pyrrolidin-1-yl)phenyl2,3-dihydroimidazo[2,1-b]thiazole, mp 218–220 (dec). Analyzed for C15 H17 N3 S, Calculated, C: 66.39, H: 6.31, N: 15.48; Found, C: 66.30, H: 6.32, N: 15.27.

The above described pyrrolidine was treated with pyridine and ethyl chloroformate as described in Example 1(B) to afford 5-(N-ethoxycarbonyl 1,1-dihydro-4-pyridyl)-6-(4-(pyrrolidin-1-yl)phenyl-2,3-dihydroimidazo[2,1-b]thiazole.

EXAMPLE 9

5-bromo-6-(4-fluorophenyl)-2,3-dihydroimidazo[1,2-b]thiazole (1.0 mmol, 300 mg, 1 equiv) was weighed into a 50 mL airlessware flask. The flask was fitted with a stir bar and was kept under a constant flow of dry nitrogen. Tetrahydrofuran (THF, 15 mL, freshly distilled from sodium/benzophenone) was added and stirring was begun. The reaction mixture was cooled to −78° C. in a dry ice/acetone bath. Butyllithium (1.0 mmol, 2.0M in hexane) was added via syringe in a dropwise manner. The solution was allowed to warm to −30° C. over a 45-minute period, and then held at that temperature for 10 minutes. The solution was then cooled to −50° C., and magnesium bromide etherate (2 mmol, 516 mg. 2 equiv) was added as a solid. The solution was allowed to warm to 0° C. over a 30-minute period and held at that temperature for 15 minutes. The reaction mixture was then cooled to −20° C., copper iodide (20 mg) added, and the mixture maintained at −20° C. for 10 minutes, after which dry pyridine (2.0 mmol, 158 mg) was added. After an additional 10 minutes, ethyl chloroformate (1.1 mmol, 119 mg) was added in a dropwise manner. The solution was stirred for 1 hour, during which it was allowed to warm to 20° C. The reaction was then quenched with saturated ammonium chloride/water (2.0 mL) and poured into water (100 mL). The water was extracted with methylene chloride (3×50 mL), the organic layer dried over sodium sulfate (anhydrous), and the solvent removed in vacuo to yield a yellow oil which was a mixture of 6-(4-fluorophenyl)-2,3-dihydroimidazo[2,1-b]thiazole and 5-(N-ethoxycarbonyl-1,4-dihydro-4-pyridyl)-6-(4-fluorophenyl)-2,3-dihydroimidazo[2,1-b]thiazole (260 mg of oil). The latter compound can be purified by silica gel chromatography (solvent =ether/hexane) to provide a 30–40% yield.

EXAMPLE 10

Using acetyl bromide and 5-bromo-6-(4-chlorophenyl)-2,3-dihydroimidazo[2,1-b]thiazole in the process of Example 9 gives 5-(N-methylcarbonyl-1,4-dihydro-4-pyridyl)-6-(4-chlorophenyl)-2,3-dihydroimidazo[2,1-b]thiazole.

Using benzyl chloroformate and 5-chloro-6-phenyl-2,3-dihydroimidazo[2,1-b]thiazole gives 5-(N-benzyloxycarbonyl-1,4-dihydro-4-pyridyl)-6-phenyl-2,3-dihydroimidazo[2,1-b]thiazole.

Using methyl chloroformate and 5-bromo-6-(2-methyl-phenyl)-2,3-dihydroimidazo[2,1-b]thiazole gives 5-(N-methoxycarbonyl-1,4-dihydro-4-pyridyl)-6-(2-methylphenyl)-2,3-dihydroimidazo[2,1-b]thiazole.

Using 6-bromo-7-(4-fluorophenyl)-2,3-dihydro-4H-imidazo[2,1-b]-)1,3)thiazine in the process of Example 9 gives 6-(N-ethoxycarbonyl-1,4-dihydro-4-pyridyl)7-(4-fluorophenyl)-2,3-dihydro-4H-imidazo[2,1-b]-(1,3)thiazine.

What is claimed is:

1. A compound of the formula

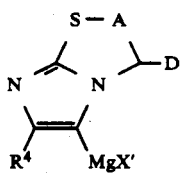

in which:
A is a methylene group optionally substituted by methyl, ethyl or gem-dimethyl, or A is a 1,2-ethanediyl group optionally substituted by methyl, ethyl or gem-dimethyl on either or both carbon atoms of the 1,2-ethandiyl group;
D is H, methyl, ethyl, or gem-dimethyl;
$R^4$ is
 (a) phenyl;
 (b) monosubstituted phenyl wherein the substituent is halogen, $C_1$–$C_3$ alkoxy, $C_1$–$C_3$ alkylthio, $C_1$–$C_4$ alkyl, $CF_3$, 2,2,2-triethoxy, prop-2-ene-1-oxy $C_1$–$C_3$ dialkylamino, pyrrolidino or piperidino, or $R^a C(O)N(CH_2)_n CH_3$ wherein $R^a$ is H, $CH_3$, $CH_2 CH_3$ and n is 0 to 2;
 (c) disubstituted phenyl wherein the substituents are independently $C_1$–$C_4$ alkyl or $C_1$–$C_3$ alkoxy, or the substituents together form a methylenedioxy group; or
 (d) 3,4,5-trimethoxyphenyl; and X, is Cl, Br, or I.

2. The compound of claim 1 in which $R^4$ is phenyl or phenyl monosubstituted with halogen, $C_1$–$C_2$ alkyl, $CF_3$, pyrrocidino or piperidino.

3. The compound of claim 2 in which X' is Br.

4. The compound of claim 1 in which A is an unsubstituted methylene and D is hydrogen.

5. The compound of claim 1 in which A is an unsubstituted 1,2ethanediyl and D is hydrogen.

* * * * *